United States Patent [19]

Unger et al.

[11] Patent Number: 5,348,016
[45] Date of Patent: Sep. 20, 1994

[54] APPARATUS FOR PREPARING GAS FILLED LIPOSOMES FOR USE AS ULTRASONIC CONTRAST AGENTS

[76] Inventors: Evan C. Unger, 13365 E. Camino La Cebadilla; Guanli Wu, 2602 W. Aiden St., both of Tucson, Ariz. 85749

[21] Appl. No.: 88,268

[22] Filed: Jul. 7, 1993

Related U.S. Application Data

[60] Division of Ser. No. 17,683, Feb. 12, 1993, which is a division of Ser. No. 717,084, Jun. 18, 1991, Pat. No. 5,228,446, and a continuation-in-part of Ser. No. 569,828, Aug. 20, 1990, Pat. No. 5,088,499, which is a continuation-in-part of Ser. No. 455,707, Dec. 22, 1989, abandoned.

[51] Int. Cl.$^5$ .................... A61B 8/00; B01J 13/02
[52] U.S. Cl. ................... 128/662.02; 264/4.6; 436/829
[58] Field of Search .................. 436/829; 128/662.02; 264/4.1, 4.6; 428/402.2; 424/450

[56] References Cited

U.S. PATENT DOCUMENTS

| | | | |
|---|---|---|---|
| 4,310,505 | 1/1982 | Baldeschwieler et al. | 424/1 |
| 4,728,575 | 3/1988 | Gamble et al. | 428/402.2 |
| 4,921,706 | 5/1990 | Roberts et al. | 424/450 |

FOREIGN PATENT DOCUMENTS

| | | |
|---|---|---|
| 63-60943 | 3/1988 | Japan. |
| WO93/05819 | 4/1993 | PCT Int'l Appl. |
| WO93/06869 | 4/1993 | PCT Int'l Appl. |
| WO93/20802 | 10/1993 | PCT Int'l Appl. |

OTHER PUBLICATIONS

Gregoriadis, G. "Preparation of Liposomes", Liposome Technology (Textbook) CRC Press, Boca Raton Fla. 1984 vol. 1 p. 34.

*Primary Examiner*—Francis Jaworski
*Attorney, Agent, or Firm*—Woodcock Washburn Kurtz Mackiewicz & Norris

[57] ABSTRACT

Contrast agents for ultrasonic imaging comprising gas filled liposomes prepared using vacuum drying gas instillation methods, and gas filled liposomes substantially devoid of liquid in the interior thereof, are described. Methods of and apparatus for preparing such liposomes and methods for employing such liposomes in ultrasonic imaging applications are also disclosed. Also described are diagnostic kits for ultrasonic imaging which include the subject contrast agents.

14 Claims, 2 Drawing Sheets

APPARATUS FOR PREPARING GAS FILLED LIPOSOMES FOR USE AS ULTRASONIC CONTRAST AGENTS

This application is a divisional application of U.S. Ser. No. 017,683 filed Feb. 12, 1993, which in turn is a divisional of U.S. Ser. No. 717,084 filed on Jun. 18, 1991 and now U.S. Pat. No. 5,228,446, which in turn is a continuation-in-part of copending application U.S. Ser. No. 569,828, filed Aug. 20, 1990 and now U.S. Pat. No. 5,088,499, which in turn is a continuation-in-part of application U.S. Ser. No. 455,707, filed Dec. 22, 1989 and now abandoned, the disclosures of each of which are incorporated herein by reference in their entirety.

BACKGROUND OF THE INVENTION

1. Field of the Invention

This invention relates to the field of ultrasonic imaging and, more specifically, to gas filled liposomes prepared using vacuum drying gas instillation methods, and to gas filled liposomes substantially devoid of liquid in the interior thereof. The invention also relates to methods of and apparatus for preparing such liposomes and to methods for employing such liposomes in ultrasonic imaging applications.

2. Background of the Invention

There are a variety of imaging techniques which have been used to detect and diagnose disease in animals and humans. One of the first techniques used for diagnostic imaging was X-rays. The images obtained through this technique reflect the electron density of the object being imaged. Contrast agents such as barium or iodine have been used over the years to attenuate or block X-rays such that the contrast between various structures is increased. For example, barium is used for gastro-intestinal studies to define the bowel lumen and visualize the mucosal surfaces of the bowel. Iodinated contrast media is used intravascularly to visualize the arteries in an X-ray process called angiography. X-rays, however, are known to be somewhat dangerous, since the radiation employed in X-rays is ionizing, and the various deleterious effects of ionizing radiation are cumulative.

Magnetic resonance imaging (MRI) is another important imaging technique, however, this technique has various drawbacks such as expense and the fact that it cannot be conducted as a portable examination. In addition, MRI is not available at many medical centers.

Radionuclides, employed in nuclear medicine, provide a further imaging technique. In employing this technique, radionuclides such as technetium labelled compounds are injected into the patient, and images are obtained from gamma cameras. Nuclear medicine techniques, however, suffer from poor spatial resolution and expose the animal or patient to the deleterious effects of radiation. Furthermore, there is a problem with the handling and disposal of radionuclides.

Ultrasound, a still further diagnostic imaging technique, is unlike nuclear medicine and X-rays in that it does not expose the patient to the harmful effects of ionizing radiation. Moreover, unlike magnetic resonance imaging, ultrasound is relatively inexpensive and can be conducted as a portable examination. In using the ultrasound technique, sound is transmitted into a patient or animal via a transducer. When the sound waves propagate through the body, they encounter interfaces from tissues and fluids. Depending on the acoustic properties of the tissues and fluids in the body, the ultrasound sound waves are partially or wholly reflected or absorbed. When sound waves are reflected by an interface they are detected by the receiver in the transducer and processed to form an image. The acoustic properties of the tissues and fluids within the body determine the contrast which appears in the resultant image.

Advances have been made in recent years in ultrasound technology. However, despite these various technological improvements, ultrasound is still an imperfect tool in a number of respects, particularly with regard to the imaging and detection of disease in the liver and spleen, kidneys, heart and vasculature, including measuring blood flow. The ability to detect and measure these things depends on the difference in acoustic properties between tissues or fluids and the surrounding tissues or fluids. As a result, contrast agents have been sought which will increase the acoustic difference between tissues or fluids and the surrounding tissues or fluids in order to improve ultrasonic imaging and disease detection.

The principles underlying image formation in ultrasound have directed researchers to the pursuit of gaseous contrast agents. Changes in acoustic properties or acoustic impedance are most pronounced at interfaces of different substances with greatly differing density or acoustic impedance, particularly at the interface between solids, liquids and gases. When ultrasound sound waves encounter such interfaces, the changes in acoustic impedance result in a more intense reflection of sound waves and a more intense signal in the ultrasound image. An additional factor affecting the efficiency or reflection of sound is the elasticity of the reflecting interface. The greater the elasticity of this interface, the more efficient the reflection of sound. Substances such as gas bubbles present highly elastic interfaces. Thus, as a result of the foregoing principles, researchers have focused on the development of ultrasound contrast agents based on gas bubbles or gas containing bodies. However, despite the theoretical reasons why such contrast agents should be effective, overall tile diagnostic results to date have been somewhat disappointing.

New and/or better contrast agents for ultrasound imaging are needed. The present invention is directed to addressing these and/or other important needs.

SUMMARY OF THE INVENTION

The present invention provides contrast agents for ultrasonic imaging.

Specifically, in one embodiment, the present invention provides ultrasound contrast agents comprising gas filled liposomes prepared by vacuum drying gas instillation methods, such liposomes sometimes being referred to herein as vacuum dried gas instilled liposomes.

In another embodiment, the invention is directed to contrast agents comprising gas filled liposomes substantially devoid of liquid in the interior thereof.

In a further embodiment, the subject invention provides methods for preparing the liposomes of the subject invention, said methods comprising: (i) placing liposomes under negative pressure; (ii) incubating the liposomes under the negative pressure for a time sufficient to remove substantially all liquid from the liposomes; and (iii) instilling selected gas into the liposomes until ambient pressures are achieved. Methods employing the foregoing steps are referred to herein as the vacuum drying gas instillation methods.

In a still further embodiment, the invention provides apparatus for preparing the liposomes of the invention using the vacuum drying gas instillation methods, said apparatus comprising: (i) a vessel containing liposomes; (ii) means for applying negative pressure to the vessel to draw liquid from the liposomes contained therein; (iii) a conduit connecting the negative pressurizing means to the vessel, the conduit directing the flow of said liquid; and (iv) means for introducing a gas into the liposomes in the vessel.

In additional embodiments, the invention contemplates methods for providing an image of an internal region of a patient, and/or for diagnosing the presence of diseased tissue in a patient, comprising: (i) administering to the patient the liposomes of the present invention; and (ii) scanning the patient using ultrasonic imaging to obtain visible images of the region of the patient, and/or of any diseased tissue in the patient.

Finally, the present invention provides diagnostic kits for ultrasonic imaging which include the contrast agents of the invention.

Surprisingly, the gas filled liposomes prepared by the vacuum drying gas instillation method, and the gas filled liposomes substantially devoid of liquid in the interior thereof which may be prepared in accordance with the vacuum drying gas instillation method, possess a number of unexpected, but highly beneficial, characteristics. The liposomes of the invention exhibit intense echogenicity on ultrasound, are highly stable to pressure and/or possess a long storage life, either when stored dry or suspended in a liquid medium. Also surprising is the ability of the liposomes during the vacuum drying gas instillation process to fill with gas and resume their original circular shape, rather than irreversibly collapse into a cup-like shape.

Indeed, despite the theoretical reasons why the prior art ultrasound contrast agents based on gas bubbles or gas containing bodies should be effective, the diagnostic results had remained largely disappointing. A number of the gaseous ultrasound contrast agents developed by prior researchers involved unstabilized bubbles, and it has been found that the instability of these contrast agents severely diminishes the diagnostic usefulness of such agents. Other gaseous ultrasound contrast agents developed by prior researchers have involved gas bubbles stabilized in constructs which also contain a substantial amount of liquid, and it has been found that the presence of a substantial amount of liquid in the construct leads to less satisfactory diagnostic results. Indeed, the presence of liquid in the construct has been found to disadvantageously alter the resonant characteristics of the gas in the construct, and has been found to hasten the diffusion of further liquid into (and concomitantly gas out of) the construct. The present invention provides new and/or better contrast agents for ultrasound imaging in an effort to address these and/or other important needs.

These and other features of the invention and the advantages thereof will be set forth in greater detail in the figures and the description below.

DETAILED DESCRIPTION OF THE INVENTION

The present invention is directed to ultrasound contrast agents comprising gas filled liposomes prepared by vacuum drying gas instillation methods, such liposomes sometimes being referred to herein as vacuum dried gas instilled liposomes. The present invention is further directed to contrast agents comprising gas filled liposomes substantially devoid of liquid in the interior thereof.

The vacuum drying gas instillation method which may be employed to prepare both the gas filled liposomes prepared by the vacuum drying gas instillation method, and the gas filled liposomes substantially devoid of liquid in the interior thereof, contemplates the following process. First, in accordance with the process, the liposomes are placed under negative pressure (that is, reduced pressure or vacuum conditions). Next, the liposomes are incubated under that negative pressure for a time sufficient to remove substantially all liquid from the liposomes, thereby resulting in substantially dried liposomes. By removal of substantially all liquid, and by substantially dried liposomes, as those phrases are used herein, it is meant that the liposomes are at least about 90% devoid of liquid, preferably at least about 95% devoid of liquid, most preferably about 100% devoid of liquid. Finally, the liposomes are instilled with selected gas by applying the gas to the liposomes until ambient pressures are achieved, thus resulting in the subject vacuum dried gas instilled liposomes of the present invention, and the gas filled liposomes of the invention substantially devoid of liquid in the interior thereof. By substantially devoid of liquid in the interior thereof, as used herein, it is meant liposomes having an interior that is at least about 90% devoid of liquid, preferably at least about 95% devoid of liquid, most preferably about 100% devoid of liquid.

Figure 2:
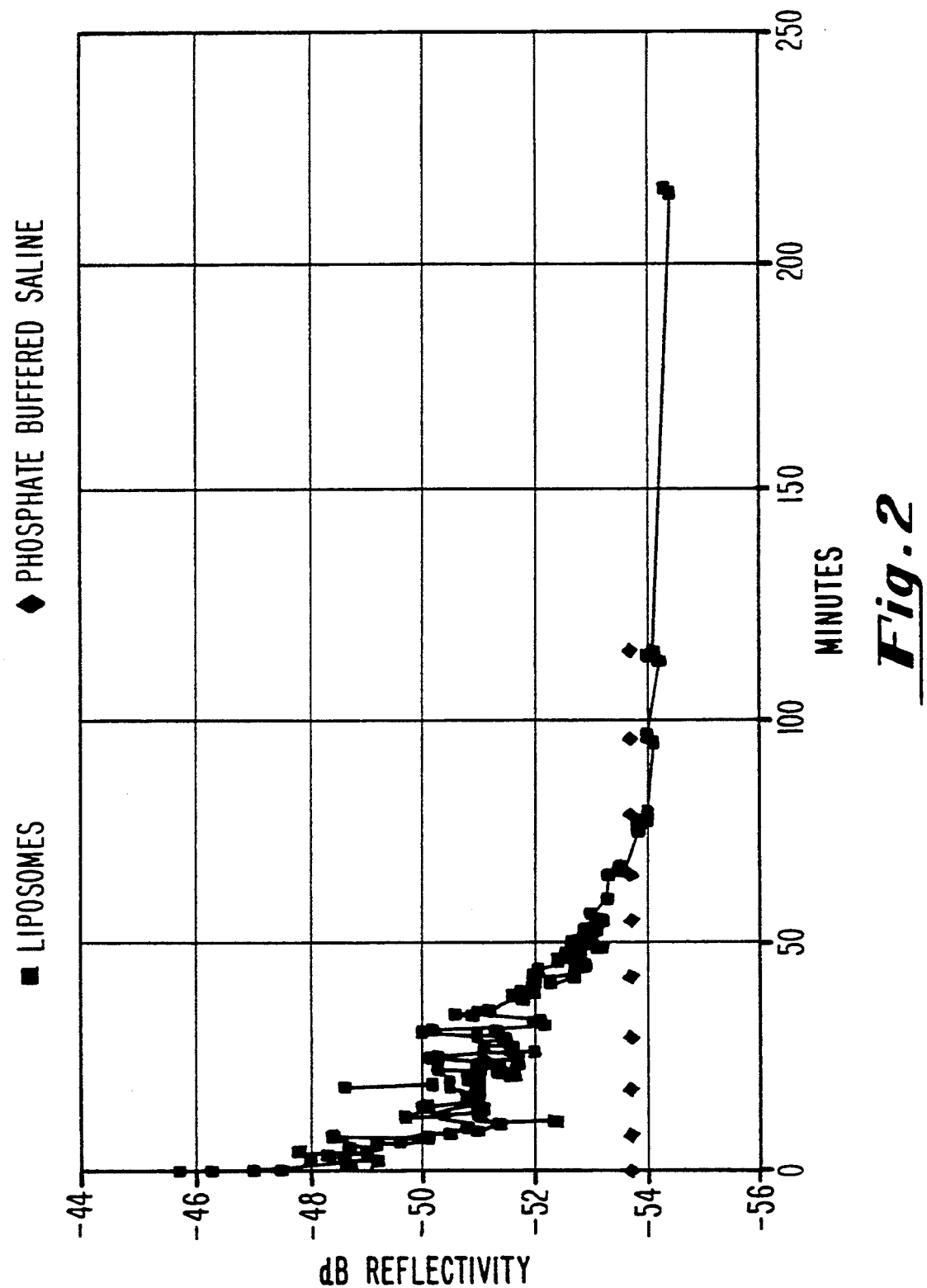
FIG. 2 is a graphical representation of the dB reflectivity of gas filled liposomes substantially devoid of liquid in the interior thereof prepared by the vacuum drying gas instillation method. The data was obtained by scanning with a 7.5 megahertz transducer using an Acoustic Imaging TM Model 5200 scanner (Acoustic Imaging, Phoenix, Ariz.), and was generated by using the system test software to measure reflectivity. The system was standardized prior to each experiment with a phantom of known acoustic impedance.

Unexpectedly, the liposomes prepared in accordance with the vacuum dried gas instillation method, and the gas filled liposomes, substantially devoid of liquid in the interior thereof, possess a number of surprising yet highly beneficial characteristics. The liposomes of the invention exhibit intense echogenicity on ultrasound, are highly stable to pressure, and/or generally possess a long storage life, either when stored dry or suspended in a liquid medium. The ecogenicity of the liposomes is of obvious importance to the diagnostic applications of the invention, and is illustrated in FIG. 2. Preferably, the liposomes of the invention possess a reflectivity of greater than 2 dB, preferably between about 4 dB and about 20 dB. Within these ranges, the highest reflectivity for the liposomes of the invention is exhibited by the larger liposomes, by higher concentrations of liposomes, and/or where higher ultrasound frequencies are employed. The stability of the liposomes is also of great practical importance. The subject liposomes tend to have greater stability during storage than other gas filled liposomes produced via known procedures such as pressurization or other techniques. At 72 hours after formation, for example, conventionally prepared liposomes often are essentially devoid of gas, the gas having diffused out of the liposomes and/or the liposomes having ruptured and/or fused, resulting in a concomitant loss in reflectivity. In comparison, gas filled liposomes of the present invention generally have a shelf life stability of greater than about three weeks, preferably a shelf life stability of greater than about four weeks, more preferably a shelf life stability of greater than about five weeks, even more preferably a shelf life stability of greater than about three months, and often a shelf life stability that is even much longer, such as over six months, twelve months, or even two years.

Also unexpected is the ability of the liposomes during the vacuum drying gas instillation process to fill with gas and resume their original circular shape, rather than collapse into a cup-shaped structure, as the prior art would cause one to expect. See, e.g., Crowe et al., *Archives of Biochemistry and Biophysics*, Vol. 242, pp. 240–247 (1985); Crowe et al., *Archives of Biochemistry and Biophysics*, Vol. 220, pp. 477–484 (1983); Fukuda et al., *J. Am. Chem. Soc.*, Vol. 108, pp. 2321–2327 (1986); Regen et al., *J. Am. Chem. Soc.*, Vol. 102, pp. 6638–6640 (1980).

The liposomes subjected to the vacuum drying gas instillation method of the invention may be prepared using any one of a variety of conventional liposome preparatory techniques which will be apparent to those skilled in the art. These techniques include freeze-thaw, as well as techniques such as sonication, chelate dialysis, homogenization, solvent infusion, microemulsification, spontaneous formation, solvent vaporization, French pressure cell technique, controlled detergent dialysis, and others. The size of the liposomes can be adjusted, if desired, prior to vacuum drying and gas instillation, by a variety of procedures including extrusion, filtration, sonication, homogenization, employing a laminar stream of a core of liquid introduced into an immiscible sheath of liquid, and similar methods, in order to modulate resultant liposomal biodistribution and clearance. Extrusion under pressure through pores of defined size is, however, the preferred means of adjusting the size of the liposomes. The foregoing techniques, as well as others, are discussed, for example, in U.S. Pat. No. 4,728,578; U.K. Patent Application GB 2193095 A; U.S. Pat. No. 4,728,575; U.S. Pat. No. 4,737,323; International Application PCT/US85/01161; Mayer et al., *Biochimica et Biophysica Acta*, Vol. 858, pp. 161–168 (1986); Hope et al., *Biochimica et Biophysica Acta*, Vol. 812, pp. 55–65 (1985); U.S. Pat. No. 4,533,254; Mayhew et al., *Methods in Enzymology*, Vol. 149, pp. 64–77 (1987); Mayhew et al., *Biochimica et Biophysica Acta*, Vol 755, pp. 169–74 (1984); Cheng et al, *Investigative Radiology*, Vol. 22, pp. 47–55 (1987); PCT/US89/05040; U.S. Pat. No. 4,162,282; U.S. Pat. No. 4,310,505; U.S. Pat. No. 4,921,706; and *Liposomes Technology*, Gregoriadis, G., ed., Vol. I, pp. 29–37, 51–67 and 79–108 (CRC Press Inc, Boca Raton, Fla., 1984). The disclosures of each of the foregoing patents, publications and patent applications are incorporated by reference herein, in their entirety. Although any of a number of varying techniques can be employed, preferably the liposomes are prepared via microemulsification techniques. The liposomes produced by the various conventional procedures can then be employed in the vacuum drying gas instillation method of the present invention, to produce the liposomes of the present invention.

The materials which may be utilized in preparing liposomes to be employed in the vacuum drying gas instillation method of the present invention include any of the materials or combinations thereof known to those skilled in the art as suitable for liposome construction. The lipids used may be of either natural or synthetic origin. Such materials include, but are not limited to, lipids such as fatty acids, lysolipids, dipalmitoylphosphatidylcholine, phosphatidylcholine, phosphatidic acid, sphingomyelin, cholesterol, cholesterol hemisuccinate, tocopherol hemisuccinate, phosphatidylethanolamine, phosphatidylinositol, lysolipids, sphingomyelin, glycosphingolipids, glucolipids, glycolipids, sulphatides, lipids with ether and ester-linked fatty acids, polymerized lipids, diacetyl phosphate, stearylamine, distearoylphosphatidylcholine, phosphatidylserine, sphingomyelin, cardiolipin, phospholipids with short chain fatty acids of 6–8 carbons in length, synthetic phospholipids with asymmetric acyl chains (e.g., with one acyl chain of 6 carbons and another acyl chain of 12 carbons), 6-(5-cholesten-3$\beta$-yloxy)-1-thio-$\beta$-D-galactopyranoside, digalactosyldiglyceride, 6-(5-cholesten-3$\beta$-yloxy)hexyl-6-amino-6-deoxy-1-thio-$\beta$-D-galactopyranoside, 6-(5-cholesten-3$\beta$-yloxy)hexyl-6-amino-6-deoxyl-1-thio-$\alpha$-D-mannopyranoside, dibehenoylphosphatidylcholine, dimyristoylphosphatidylcholine, dilauroylphosphatidylcholine, and dioleoylphosphatidylcholine, and/or combinations thereof. Other useful lipids or combinations thereof apparent to those skilled in the art which are in keeping with the spirit of the present invention are also encompassed by the present invention. For example, carbohydrates bearing lipids may be employed for in vivo targeting as described in U.S. Pat. No. 4,310,505. Of particular interest for use in the present invention are lipids which are in the gel state (as compared with the liquid crystalline state) at the temperature at which the vacuum drying gas instillation is performed. The phase transition temperatures of various lipids will be readily apparent to those skilled in the art and are described, for example, in *Liposome Technology*, Gregoriadis, G., ed., Vol. I, pp. 1–18 (CRC Press, Inc. Boca Raton, Fla. 1984), the disclosures of which are incorporated herein by reference in their entirety. In addition, it has been found that the incorporation of at least a small amount of negatively charged lipid into any liposome membrane, although not required, is beneficial to providing highly stable liposomes. By at least a small amount, it is meant about 1 mole percent of the total lipid. Suitable negatively charged lipids will be readily apparent to those skilled in the art, and include, for example phosphatidylserine and fatty acids. Most preferred for reasons of the combined ultimate ecogenicity and stability following the vacuum drying gas instillation process are liposomes prepared from dipalmitoylphosphatidylcholine.

By way of general guidance, dipalmitoylphosphatidylcholine liposomes may be prepared by suspending dipalmitoylphosphatidylcholine lipids in phosphate buffered saline or water, and heating the lipids to about 50° C., a temperature which is slightly above the 45° C. temperature required for transition of the dipalmitoylphosphatidylcholine lipids from a gel state to a liquid crystalline state, to form liposomes. To prepare multilamellar vesicles of a rather heterogeneous size distribution of around 2 microns, the liposomes may then be mixed gently by hand while keeping the liposome solution at a temperature of about 50° C. The temperature is then lowered to room temperature, and the liposomes remain intact. Extrusion of dipalmitoylphosphatidylcholine liposomes through polycarbonate filters of defined size may, if desired, be employed to make liposomes of a more homogeneous size distribution. A device useful for this technique is an extruder device (Extruder Device TM, Lipex Biomembranes, Vancouver, Canada) equipped with a thermal barrel so that extrusion way be conveniently accomplished above the gel state-liquid crystalline transition temperature for lipids.

Alternatively, and again by way of general guidance, conventional freeze-thaw procedures way be used to produce either oligolamellar or unilamellar dipalmitoylphosphatidylcholine liposomes. After the freeze-thaw procedures, extrusion procedures as described above may then be performed on the liposomes.

The liposomes thus prepared may then be subjected to the vacuum drying gas instillation process of the present invention, to produce the vacuum dried gas instilled liposomes, and the gas filled liposomes substantially devoid of liquid in the interior thereof, of the invention. In accordance with the process of the invention, the liposomes are placed into a vessel suitable for subjecting to the liposomes to negative pressure (that is, reduced pressure or vacuum conditions). Negative pressure is then applied for a time sufficient to remove substantially all liquid from the liposomes, thereby resulting in substantially dried liposomes. As those skilled in the art would recognize, once armed with the present disclosure, various negative pressures can be employed, the important parameter being that substantially all of the liquid has been removed from the liposomes. Generally, a negative pressure of at least about 700 mm Hg preferably in the range of between about 700 mm Hg and about 760 mm Hg (gauge pressure), applied for about 24 to about 72 hours, is sufficient to remove substantially all of the liquid from the liposomes. Other suitable pressures and time periods will be apparent to those skilled in the art, in view of the disclosures herein.

Finally, a selected gas is applied to the liposomes to instill the liposomes with gas until ambient pressures are achieved, thereby resulting in the vacuum dried gas instilled liposomes of the invention, and in the gas filled liposomes substantially devoid of liquid in the interior thereof. Preferably, gas instillation occurs slowly, that is, over a time period of at least about 4 hours, most preferably over a time period of between about 4 and about 8 hours. Various biocompatible gases may be employed. Such gases include air, nitrogen, carbon dioxide, oxygen, argon, xenon, neon, helium, or any and all combinations thereof. Other suitable gases will be apparent to those skilled in the art, the gas chosen being only limited by the proposed application of the liposomes.

The above described method for production of liposomes is referred to hereinafter as the vacuum drying gas instillation process.

If desired, the liposomes may be cooled, prior to subjecting the liposomes to negative pressure, and such cooling is preferred. Preferably, the liposomes are cooled to below 0° C., more preferably to between about −10° C. and about −20° C., and most preferably to −10° C., prior to subjecting the liposomes to negative pressure. Upon reaching the desired negative pressure, the liposomes temperature is then preferably increased to above 0° C., more preferably to between about 10° C. and about 20° C., and most preferably to 10° C., until substantially all of the liquid has been removed from the liposomes and the negative pressure is discontinued, at which time the temperature is then permitted to return to room temperature.

If the liposomes are cooled to a temperature below 0° C., it is preferable that the vacuum drying gas instillation process be carried out with liposomes either initially prepared in the presence of cryoprotectants, or liposomes to which cryoprotectants have been added prior to carrying out the vacuum drying gas instillation process of the invention. Such cryoprotectants, while not mandatorily added, assist in maintaining the integrity of liposome membranes at low temperatures, and also add to the ultimate stability of the membranes. Preferred cryoprotectants are trehalose, glycerol, polyethyleneglycol (especially polyethyleneglycol of molecular weight 400), raffinose, sucrose and sorbitol, with trehalose being particularly preferred.

It has also been surprisingly discovered that the liposomes of the invention are highly stable to changes in pressure. Because of this characteristic, extrusion of the liposomes through filters of defined pore size following vacuum drying and gas instillation can be carried out, if desired, to create liposomes of relatively homogeneous and defined pore size.

For storage prior to use, the liposomes of the present invention may be suspended in an aqueous solution, such as a saline solution (for example, a phosphate buffered saline solution), or simply water, and stored preferably at a temperature of between about 2° C. and about 10° C., preferably at about 4° C. Preferably, the water is sterile. Most preferably, the liposomes are stored in a hypertonic saline solution (e.g., about 0.3 to about 0.5% NaCl), although, if desired, the saline solution may be isotonic. The solution also may be buffered, if desired, to provide a pH range of pH 6.8 to pH 7.4. Suitable buffers include, but are not limited to, acetate, citrate, phosphate and bicarbonate. Dextrose may also be included in the suspending media. Preferably, the aqueous solution is degassed (that is, degassed under vacuum pressure) prior to suspending the liposomes therein. Bacteriostatic agents may also be included with the liposomes to prevent bacterial degradation on storage. Suitable bacteriostatic agents include but are not limited to benzalkonium chloride, benzethonium chloride, benzoic acid, benzyl alcohol, butylparaben, cetylpyridinium chloride, chlorobutanol chlorocresol, methylparaben, phenol, potassium benzoate, potassium sorbate, sodium benzoate and sorbic acid. One or more antioxidants may further be included with the gas filled liposomes to prevent oxidation of the lipid. Suitable antioxidants include tocopherol, ascorbic acid and ascorbyl palmitate. Liposomes prepared in the various foregoing manners may be stored for at least several weeks or months. Liposomes of the present invention may alternatively, if desired, be stored in their dried, unsuspended form, and such liposomes also have a shelf life of greater than several weeks or months. Specifically, the liposomes of the present invention, stored either way, generally have a shelf life stability of greater than about three weeks, preferably a shelf life stability of greater than about four weeks, more preferably a shelf life stability of greater than about five weeks, even more preferably a shelf life stability of greater than about three months, and often a shelf life stability that is even much longer, such as over six months, twelve months or even two years.

Figure 1:
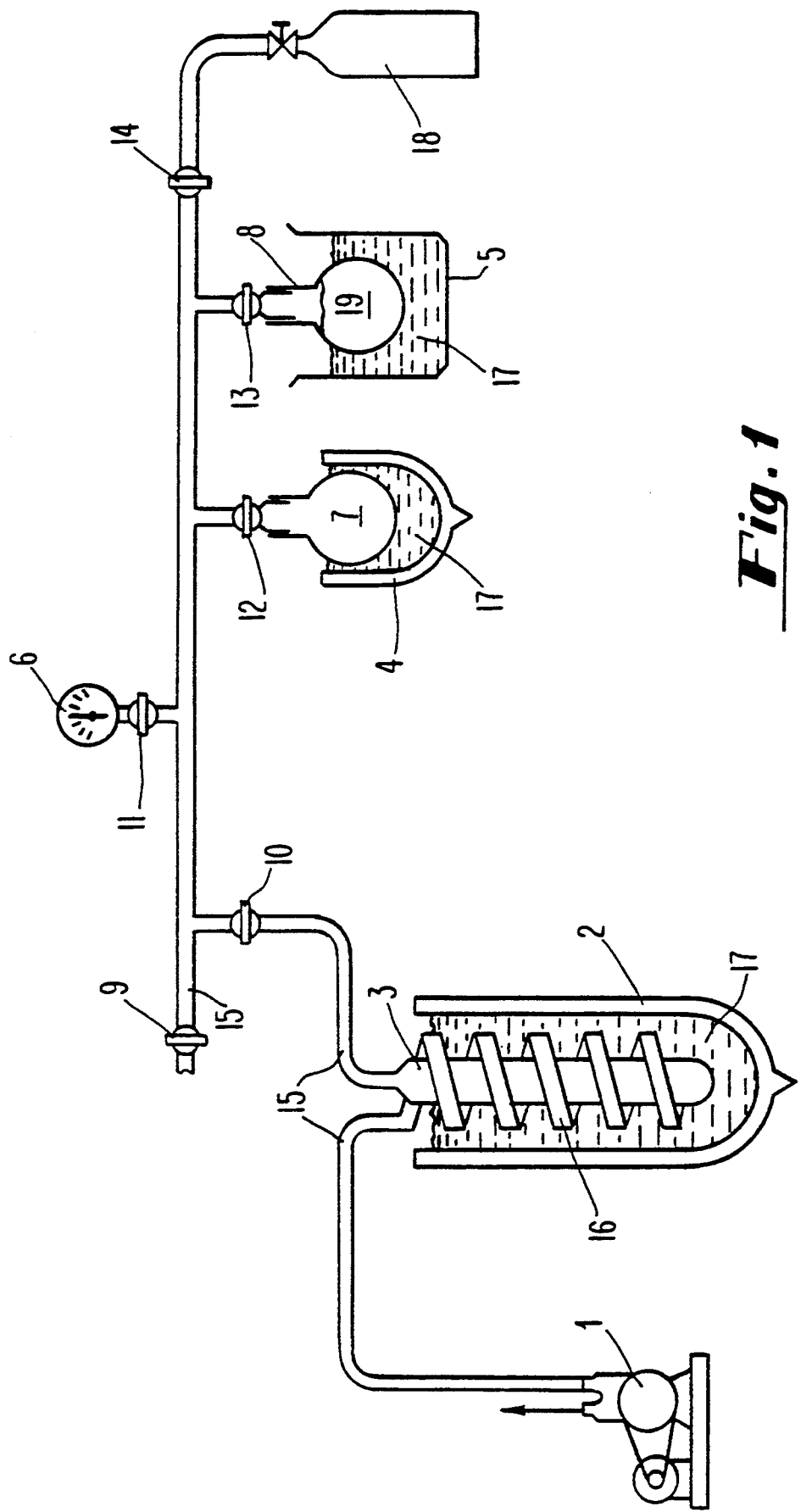
FIG. 1 shows an apparatus according to the present invention for preparing the vacuum dried gas instilled liposomes and the gas filled liposomes substantially devoid of liquid in the interior thereof prepared by the vacuum drying gas instillation method.

As another aspect of the invention, useful apparatus for preparing the vacuum dried gas instilled liposomes, and the gas filled liposomes substantially devoid of liquid in the interior thereof, of the invention is also presented. Specifically, there is shown in FIG. 1 a preferred apparatus for vacuum drying liposomes and instilling a gas into the dried liposomes. The apparatus is comprised of a vessel 8 for containing liposomes 19. If desired, the apparatus may include an ice bath 5 containing dry ice 17 surrounding the vessel 8. The ice bath 5 and dry ice 17 allow the liposomes to be cooled to below 0° C. A vacuum pump 1 is connected to the vessel 8 via a conduit 15 for applying a sustained negative pressure to the vessel. In the preferred embodiment, the pump 1 is capable of applying a negative pressure of at least about 700 mm Hg, and preferably a negative pressure in the range of about 700 mm Hg to about 760 mm Hg (gauge pressure). A manometer 6 is connected to the conduit 15 to allow monitoring of the negative pressure applied to the vessel 8.

In order to prevent liquid removed from the liposomes from entering the pump 1, a series of traps are connected to the conduit 15 to assist in collecting the liquid (and liquid vapor, all collectively referred to herein as liquid) drawn from the liposomes. In a preferred embodiment, two traps are utilized. The first trap is preferably comprised of a flask 7 disposed in an ice bath 4 with dry ice 17. The second trap is preferably comprised of a column 3 around which tubing 16 is helically arranged. The column 3 is connected to the conduit 15 at its top end and to one end of the tubing 16 at its bottom end. The other end of the tubing 16 is connected to the conduit 15. As shown in FIG. 1, an ice bath 2 with dry ice 17 surrounds the column 3 and tubing 16. If desired, dry ice 17 can be replaced with liquid nitrogen, liquid air or other cryogenic material. The ice baths 2 and 4 assist in collecting any liquid and condensing any liquid vapor drawn from the liposomes for collection in the traps. In preferred embodiments of the present invention the ice traps 2 and 4 are each maintained at a temperature of least about $-70°$ C.

A stopcock 14 is disposed in the conduit 15 upstream of the vessel 8 to allow a selected gas to be introduced into the vessel 8 and into the liposomes 19 from gas bottle 18.

Apparatus of the present invention are utilized by placing the liposomes 19 into vessel 8. In a preferable embodiment, ice bath 5 with dry ice 17 is used to lower the temperature of the liposomes to below 0° C., more preferably to between about $-10°$ C. and about $-20°$ C., and most preferably to $-10°$ C. With stopcocks 14 and 9 closed, vacuum pump 1 is turned on. Stopcocks 10, 11, 12 and 13 are then carefully opened to create a vacuum in vessel 8 by means of vacuum pump 1. The pressure is gauged by means of manometer 6 until negative pressure of at least about 700 mm Hg and preferably in the range of between about 700 mm Hg and about 760 mm Hg (gauge pressure) is achieved. In preferred embodiments of the present invention vessel 7, cooled by ice bath 4 with dry ice 17, and column 3 and coil 16, cooled by ice bath 2 with dry ice 17, together or individually condense liquid vapor and trap liquid drawn from the liposomes so as to prevent such liquids and liquid vapor from entering the vacuum pump 1. In preferred embodiments of the present invention, the temperature of ice traps 2 and 4 are each maintained at a temperature of at least about $-70°$ C. The desired negative pressure is generally maintained for at least 24 hours as liquid and liquid vapor is removed from the liposomes 19 in vessel 8 and frozen in vessels 3 and 7. Pressure within the system is monitored using manometer 6 and is generally maintained for about 24 to about 72 hours, at which time substantially all of the liquid has been removed from the liposomes. At this point, stopcock 10 is slowly closed and vacuum pump 1 is turned off. Stopcock 14 is then opened gradually and gas is slowly introduced into the system from gas bottle 18 through stopcock 14 via conduit 15 to instill gas into the liposomes 19 in vessel 8. Preferably the gas instillation occurs slowly over a time period of at least about 4 hours, most preferably over a time period of between about 4 and about 8 hours, until the system reaches ambient pressure.

The vacuum dried gas instilled liposomes and the gas filled liposomes substantially devoid of liquid in the interior thereof of the present invention have superior characteristics for ultrasound contrast imaging. Specifically, the present invention is useful in imaging a patient generally, and/or in diagnosing the presence of diseased tissue in a patient. The patient may be any type of mammal, but is most preferably human. Thus, in further embodiments of the present invention, a method of providing an image of an internal bodily region of a patient is provided. This method comprises administering the liposomes of the invention to the patient and scanning the patient using ultrasonic imaging to obtain visible images of the region. A method is also provided for diagnosing the presence of diseased tissue in a patient, said method comprising administering to a patient liposomes of the present invention, and then scanning the patient using ultrasonic imaging to obtain visible images of any diseased tissue in the patient. By region of a patient, it is meant the whole patient, or a particular area or portion of the patient. For example, by using the method of the invention, a patient's heart, and a patient's vasculature (that is, venous or arterial systems), may be visualized and/or diseased tissue may be diagnosed. In visualizing a patient's vasculature, blood flow may be measured, as will be well understood by those skilled in the art in view of the present disclosure. The invention is also particularly useful in visualizing and/or diagnosing disease in a patient's right heart, a region not easily imaged heretofore by ultrasound. Liver, spleen and kidney regions of a patient may also be readily visualized and/or disease detected therein using the present methods.

Liposomes of the present invention may be of varying sizes, but preferably are of a size range wherein they have a mean outside diameter between about 30 nanometers and about 10 microns, with the preferable mean outside diameter being about 2 microns. As is known to those skilled in the art, liposome size influences biodistribution and, therefore, different size liposomes may be selected for various purposes. For intravascular use, for example, liposome size is generally no larger than about 5 microns, and generally no smaller than about 30 nanometers, in mean outside diameter. To provide ultrasound enhancement of organs such as the liver and to allow differentiation of tumor from normal tissue, smaller liposomes, between about 30 nanometers and about 100 nanometers in mean outside diameter, are useful.

Any of the various types of ultrasound imaging devices can be employed in the practice of the invention, the particular type or model of the device not being critical to the method of the invention. Generally, for the diagnostic uses of the present invention, ultrasound frequencies between about 3.0 to about 7.5 megahertz are employed.

As one skilled in the art would recognize, administration of contrast imaging agents of the present invention may be carried out in various fashions, such as intravascularly intralymphatically, parenterally, subcutaneously, intramuscularly, intraperitoneally, interstitially, hyperbarically, orally, or intratumorly using a variety of dosage forms. One preferred route of administration is intravascularly. For intravascular use the contrast agent is generally injected intravenously, but may be injected intraarterially as well. The useful dosage to be administered and the mode of administration will vary depending upon the age, weight, and mammal to be diagnosed, and the particular diagnostic application intended. Typically dosage is initiated at lower levels and increased until the desired contrast enhancement is achieved. Generally, the contrast agents of the invention are administered in the form of an aqueous suspension such as in water or a saline solution (e.g., phosphate buffered saline). Preferably, the water is sterile. Also preferably the saline solution is a hypertonic saline solution (e.g., about 0.3 to about 0.5% NaCl), although, if desired, the saline solution may be isotonic. The solution also may be buffered, if desired, to provide a pH range of pH 6.8 to pH 7.4. In addition, dextrose may be preferably included in the media. Preferably, the aqueous solution is degassed (that is, degassed under vacuum pressure) prior to suspending the liposomes therein.

Kits useful for ultrasonic imaging in accordance with the present invention comprise gas filled liposomes prepared by a vacuum drying gas instillation methods, and gas filled liposomes substantially devoid of liquid in the interior thereof, in addition to conventional ultrasonic imaging kit components. Such conventional ultrasonic imaging kit components are well known, and include, for example, filters to remove bacterial contaminants or to break up liposomal aggregates prior to administration.

The liposomes of the present invention are believed to differ from the liposomes of the prior art in a number of respects, both in physical and in functional characteristics. For example, the liposomes of the invention are substantially devoid of liquid in the interior thereof. By definition, liposomes in the prior art have been characterized by the presence of an aqueous medium. See, e.g., *Dorland's Illustrated Medical Dictionary*, p. 946, 27th ed. (W.B. Saunders Company, Philadelphia 1988). Moreover, the present liposomes surprisingly exhibit intense ecogenicity on ultrasound, and possess a long storage life, characteristics of great benefit to the use of the liposomes as ultrasound contrast agents.

There are various other applications for liposomes of the invention, beyond those described in detail herein. Such additional uses, for example, include such applications as hyperthermia potentiators for ultrasound and as drug delivery vehicles. Such additional uses and other related subject matter are described and claimed in applicant's patent applications filed concurrently herewith entitled "Novel Liposomal Drug Delivery Systems" and "Method For Providing Localized Therapeutic Heat to Biological Tissues and Fluids Using Gas Filled Liposomes", the disclosures of each of which are incorporated herein by reference in their entirety.

The present invention is further described in the following examples. Examples 1-8 are actual examples that describe the preparation and testing of the vacuum dried gas instilled liposomes, the gas filled liposomes being substantially devoid of any liquid in the interior thereof. Examples 9-11 are prophetic examples that describe the use of the liposomes of the invention. The following examples should not be construed as limiting the scope of the appended claims.

EXAMPLES

Example 1

Dipalmitoylphosphatidylcholine (1 gram) was suspended in 10 ml phosphate buffered saline, the suspension was heated to about 50° C., and then swirled by hand in a round bottom flask for about 30 minutes. The heat source was removed, and the suspension was swirled for two additional hours, while allowing the suspension to cool to room temperature, to form liposomes.

The liposomes thus prepared were placed in a vessel in an apparatus similar to that shown in FIG. 1, cooled to about −10° C., and then subjected to high negative vacuum pressure. The temperature of the liposomes was then raised to about 10° C. High negative vacuum pressure was maintained for about 48 hours. After about 48 hours, nitrogen gas was gradually instilled into the chamber over a period of about 4 hours, after which time the pressure returned to ambient pressure. The resulting vacuum dried gas instilled liposomes, the gas filled liposomes being substantially devoid of any liquid in the interior thereof, were then suspended in 10 cc of phosphate buffered saline and stored at about 4° C. for about three months.

Example 2

To test the liposomes of Example 1 ultrasonographically, a 250 mg sample of these liposomes was suspended in 300 cc of degassed phosphate buffered saline (that is, degassed under vacuum pressure). The liposomes were then scanned in vitro at varying time intervals with a 7.5 mHz transducer using an Acoustic Imaging Model 5200 scanner (Acoustic Imaging, Phoenix, Ariz.) and employing the system test software to measure dB reflectivity. The system was standardized prior to testing the liposomes with a phantom of known acoustic impedance. A graph showing dB reflectivity is provided in FIG. 2.

Example 3

Dipalmitoylphosphatidylcholine (1 gram) and the cryoprotectant trehalose (1 gram) were suspended in 10 ml phosphate buffered saline, the suspension was heated to about 50° C., and then swirled by hand in a round bottom flask for about 30 minutes. The heat source was removed, and the suspension was swirled for about two additional hours, while allowing the suspension to cool to room temperature, to form liposomes.

The liposomes thus prepared were then vacuum dried and gas instilled, substantially following the procedures shown in Example 1, resulting in vacuum dried gas instilled liposomes, the gas filled liposomes being substantially devoid of any liquid in the interior thereof. The liposomes were then suspended in 10 cc of phosphate buffered saline, and then stored at about 4° C. for several weeks.

Example 4

To test the liposomes of Example 3 ultrasonographically, the procedures of Example 2 were substantially followed. The dB reflectivity of the liposomes were similar to the dB reflectivity reported in Example 2.

Example 5

Dipalmitoylphosphatidylcholine (1 gram) was suspended in 10 ml phosphate buffered saline, the suspension was heated to about 50° C., and then swirled by hand in a round bottom flask for about 30 minutes. The suspension was then subjected to 5 cycles of extrusion through an extruder device jacketed with a thermal barrel (Extruder Device TM, Lipex Biomembranes, Vancouver, Canada), both with and without conventional freeze-thaw treatment prior to extrusion, while maintaining the temperature at about 50° C. The heat source was removed, and the suspension was swirled for about two additional hours, while allowing the suspension to cool to room temperature, to form liposomes.

The liposomes thus prepared were then vacuum dried and gas instilled, substantially following the procedures shown in Example 1, resulting in vacuum dried gas instilled liposomes, the gas filled liposomes being substantially devoid of any liquid in the interior thereof. The liposomes were then suspended in 10 cc of phosphate buffered saline, and then stored at about 4° C. for several weeks.

Example 6

To test the liposomes of Example 5 ultrasonographically, the procedures of Example 2 were substantially followed. The dB reflectivity of the liposomes were similar to the dB reflectivity reported in Example 2.

Example 7

In order to test the stability of the liposomes of the invention, the liposomes suspension of Example 1 was passed through 2 micron polycarbonate filters in an extruder device (Extruder Device TM, Lipex Biomembranes Vancouver, Canada) five times at a pressure of about 600 psi. After extrusion treatment, the liposomes were studied ultrasonographically, as described in Example 2. Surprisingly, even after extrusion under high pressure, the liposomes of the invention substantially retained their echogenicity.

Example 8

The liposomes of Example 1 were scanned by ultrasound using transducer frequencies varying from 3 to 7.5 mHz. The results indicated that at a higher frequency of ultrasound, the echogenicity decays more rapidly, reflecting a relatively high resonant frequency and higher energy associated with the higher frequencies.

The following examples, Examples 9, 10, and 11, are prophetic examples.

Example 9

A patient with suspected myocardial ischemia is administered an intravenous dose of 500 mg of vacuum dried gas instilled liposomes encapsulating nitrogen gas, the gas filled liposomes being substantially devoid of liquid in the interior thereof, with a mean diameter of 2 microns, and the left ventricular myocardium is studied ultrasonographically.

Example 10

A patient with suspected myocardial ischemia is administered an intravenous dose of 500 mg of vacuum dried gas instilled liposomes encapsulating nitrogen gas, the gas filled liposomes being substantially devoid of liquid in the interior thereof, with a mean diameter of 2 microns, and the left ventricular myocardium is studied ultrasonographically.

Example 11

A patient with suspected hepatic metastases is administered an intravenous dose of 500 mg of vacuum dried gas instilled liposomes encapsulating nitrogen gas, the gas filled liposomes being substantially devoid of liquid in the interior thereof, and the liver is examined ultrasonographically.

Various modifications of the invention in addition to those shown and described herein will be apparent to those skilled in the art from the foregoing description. Such modifications are also intended to fall within the scope of the appended claims.

What is claimed is:

1. An apparatus for preparing contrast agents for ultrasonic imaging by drying liposomes and instilling gas therein comprising:
   (i) a vessel for containing liposomes;
   (ii) means for sequentially applying a negative pressure to the vessel for a first pre-determined period of time to draw liquid from liposomes contained in the vessel and then subsequently applying a gas to the vessel to gradually eliminate the negative pressure therein over a second pre-determined period of time, the means for sequentially applying the negative pressure and then the gas to gradually eliminate the negative pressure including (a) a vacuum source, (b) a source of pressurized gas, and (c) a conduit having means for selectively placing the vacuum source and the pressurized gas in flow communication with the vessel.

2. An apparatus of claim 1, wherein the vacuum source is a vacuum pump.

3. An apparatus according to claim 1 further comprising means for cooling the liposomes contained in the vessel.

4. An apparatus according to claim 3 wherein the cooling means has means for cooling liposomes contained in the vessel to between about −10° C. and about −20° C.

5. An apparatus according to claim 4 wherein the cooling means comprises an ice bath.

6. An apparatus according to claim 1 further comprising means for collecting the liquid drawn from the liposomes.

7. An apparatus according to claim 6 wherein the collecting means is a trap.

8. An apparatus according to claim 7 further comprising means for cooling the trap.

9. An apparatus according to claim 7 wherein the trap comprises first and second members adapted to direct fluid flow therethrough, the members in flow communication with each other and with the conduit, the second member being helically arranged around the first member, the trap comprising a cooling means wherein the cooling means comprises an ice bath enclosing at least a portion of the first and second members.

10. An apparatus for preparing contrast agents for ultrasonic imaging by drying liposomes and instilling gas therein comprising:
   (i) a vessel for containing liposomes;

(ii) means for cooling liposomes contained in the vessel to a temperature at least as low as approximately 0° C.;

(iii) means for applying a negative pressure to the vessel at least as low as approximately 700 mm Hg for a period of time at least as long as approximately 24 hours to draw liquid from the liposomes contained in the vessel;

(iv) a conduit connecting the negative pressurizing means to the vessel, the conduit directing the flow of the liquid;

(v) means for collecting the liquid flowing in the conduit; and (vi) means for isolating the negative pressurizing means from the vessel and means for thereafter gradually introducing a gas into liposomes contained in the vessel so as to gradually eliminate the negative pressure therein over a period of at least 4 hours.

11. An apparatus according to claim 10, wherein the means for thereafter gradually introducing a gas into liposomes contained in the vessel comprises a source of pressurized gas and a valve, and wherein the conduit further connects the source of pressurized gas to the vessel, said valve being disposed in said conduit.

12. An apparatus for drying liposomes and instilling gas therein comprising:

(i) a vessel for containing liposomes;

(ii) means for sequentially applying a negative pressure to the vessel for a first pre-determined period of time to draw liquid from liposomes contained in the vessel and then subsequently applying a gas to the vessel to gradually eliminate the negative pressure therein over a second pre-determined period of time, the means for sequentially applying the negative pressure and then the gas to gradually eliminate the negative pressure including (a) a vacuum source, (b) a source of pressurized gas, and (c) a conduit having means for selectively placing the vacuum source and the pressurized gas in flow communication with the vessel.

13. An apparatus for drying liposomes and instilling gas therein comprising:

(i) a vessel for containing liposomes;

(ii) means for cooling liposomes contained in the vessel to a temperature at least as low as approximately 0° C.;

(iii) means for applying a negative pressure to the vessel of at least approximately 700 mm Hg for a period of at least as long as approximately 24 hours to draw liquid from liposomes contained in the vessel;

(iv) a conduit connecting the negative pressurizing means to the vessel, the conduit directing the flow of the liquid;

(v) means for collecting the liquid flowing in the conduit; and (vi) means for isolating the negative pressurizing means from said vessel and for thereafter gradually introducing a gas into liposomes contained in said vessel so as to gradually eliminate the negative pressure therein over a period of at least 4 hours.

14. An apparatus according to claim 13, wherein the means for isolating said negative pressurizing means and for thereafter gradually introducing a gas into liposomes contained in the vessel comprises a source of pressurized gas and a valve, and wherein the conduit further connects the source of pressurized gas to the vessel, said valve being disposed in said conduit.

* * * * *

UNITED STATES PATENT AND TRADEMARK OFFICE
CERTIFICATE OF CORRECTION

PATENT NO. : 5,348,016　　　　　　　　　　　　　　　　Page 1 of 4
DATED    : Sep. 20, 1994
INVENTOR(S) : Evan C. Unger, Guanli Wu It is certified that error appears in the above-indentified patent and that said Letters Patent is hereby corrected as shown below:

On the title page, item [56], in the References Cited section, under U.S. PATENT DOCUMENTS, please add the following references:

```
--4,162,282    7/1979    Fulwyler et al. ............ 264/9--
--4,533,254    8/1985    Cook et al. .............. 366/176--
--4,586,512    5/1986    Do-huu et al. ............ 128/660--
--4,620,546   11/1986    Aida et al. .............. 128/660--
--4,658,828    4/1987    Dory ..................... 128/660--
--4,728,578    3/1988    Higgins et al. ........... 428/462--
--4,737,323    4/1988    Martin et al. ............ 264/4.3--
--4,865,836    9/1989    Long, Jr. .................. 424/5--
--4,646,756    3/1987    Watmough et al. .......... 128/804--
--4,893,624    1/1990    Lele ..................... 128/399--
--4,689,986    9/1987    Carson et al. ............... 73/19--
--4,657,756    4/1987    Rasor et al. ............... 424/9--
--4,900,540    2/1990    Ryan et al. ................ 424/9--
--4,675,310    6/1987    Chapman et al. ............. 514/6--
--4,781,871   11/1988    West, III et al. ......... 264/4.3--
```

On the first page, item [56], in the References Cited section, under FOREIGN PATENT DOCUMENTS, please add the following references:

```
--WO80/02365   11/1980   PCT Int'l Appl. .--
--WO82/01642    5/1982   PCT Int'l Appl. .--
--   0361894    4/1990   European Pat. Off. .--
--WO86/01103    2/1986   PCT Int'l Appl. .--
```

UNITED STATES PATENT AND TRADEMARK OFFICE
CERTIFICATE OF CORRECTION

PATENT NO. : 5,348,016
DATED : Sep. 20, 1994
INVENTOR(S) : Evan C. Unger, Guanli Wu It is certified that error appears in the above-indentified patent and that said Letters Patent is hereby corrected as shown below:

On the title page, item [56], in the References Cited section, under OTHER PUBLICATIONS, please add the following references:

--Cheng et al, *Investigative Radiology*, Vol. 22, pp. 47-55 (1987)--

--Crowe et al., *Archives of Biochemistry and Biophysics*, Vol. 242, pp. 240-247 (1985)--

--Crowe et al., *Archives of Biochemistry and Biophysics*, Vol. 220, pp. 477-484 (1983)--

--Dorland's Illustrated Medical Dictionary, p. 946, 27th ed. (W.B. Saunders Company, Philadelphia 1988)--

--Fukuda et al., *J. Am. Chem. Soc.*, Vol. 108, pp. 2321-2327 (1986)--

--Hope et al., *Biochimica et Biophysica Acta*, Vol. 812, pp. 55-65 (1985)--

--*Liposome Technology*, Gregoriadis, G., ed., Vol. I, pp. 1-18 (CRC Press, Inc. Boca Raton, FL 1984)--

--*Liposome Technology*, Gregoriadis, G., ed., Vol. I, pp. 29-35, 51-65 and 79-107 (CRC Press Inc, Boca Raton, FL, 1984)--

--Madden et al., *Chemistry and Physics of Lipids*, Vol. 53, pp. 37-46 (1990)--

UNITED STATES PATENT AND TRADEMARK OFFICE
CERTIFICATE OF CORRECTION

PATENT NO. : 5,348,016                        Page 3 of 4
DATED      : Sep. 20, 1994
INVENTOR(S): Evan C. Unger, Guanli Wu It is certified that error appears in the above-indentified patent and that said Letters Patent is hereby corrected as shown below:

--Mayer et al., Biochimica et Biophysica Acta, Vol. 858, pp. 161-168 (1986)--

--Mayhew et al., Methods in Enzymology, Vol. 149, pp. 64-77 (1987)--

--Regen et al., J. Am. Chem. Soc., Vol. 102, pp. 6638-6640 (1980)--

--Sinkula et al., J. Pharm. Sci., Vol. 64, pp. 181-210 (1975)--

--Shiina et al., "Hyperthermiaby Low-frequency Synthesized Ultrasound", IEEE Engineering, pp. 879-880, Vol. 2 (abstract)--

--McAvoy et al., IEEE Engineering, Ultrasonics Symposium Proceedings, Vol. 2, pp. 677-1248 (abstract)--

In column 2, line 42, please delete "tile" and insert --the-- therefor.

In column 7, line 13, please delete "way" and insert --may-- therefor.

In column 7, line 35, at the beginning of the line, before "preferably", please insert --and--.

In column 8, line 48, please insert a --,-- after "chlorobutanol".

UNITED STATES PATENT AND TRADEMARK OFFICE
CERTIFICATE OF CORRECTION

PATENT NO. : 5,348,016
DATED : Sep. 20, 1994
INVENTOR(S) : Evan C. Unger, Guanli Wu It is certified that error appears in the above-indentified patent and that said Letters Patent is hereby corrected as shown below:

In column 11, lines 6-7, please insert a --,-- after "intravascularly".

In column 13, lines 38-39, please insert a --,-- after "Biomembranes".

In column 16, claim 13, line 15, please delete "as long as".

Signed and Sealed this

Twenty-fifth Day of February, 1997

Attest:

BRUCE LEHMAN

*Attesting Officer*  *Commissioner of Patents and Trademarks*